US012766216B2

(12) United States Patent
Tkatchouk et al.

(10) Patent No.: US 12,766,216 B2
(45) Date of Patent: Oct. 20, 2026

(54) SUTURE ENCAPSULATION PROCESSES AND SYSTEMS

(71) Applicant: EDWARDS LIFESCIENCES CORPORATION, Irvine, CA (US)

(72) Inventors: Ekaterina Tkatchouk, Huntington Beach, CA (US); Maria L. Saravia, Irvine, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 350 days.

(21) Appl. No.: 18/464,230

(22) Filed: Sep. 10, 2023

(65) Prior Publication Data

US 2023/0414825 A1 Dec. 28, 2023

Related U.S. Application Data

(63) Continuation of application No. PCT/US2022/019617, filed on Mar. 9, 2022.

(60) Provisional application No. 63/159,377, filed on Mar. 10, 2021.

(51) Int. Cl.

| | |
|---|---|
| ***A61L 27/34*** | (2006.01) |
| ***A61B 17/04*** | (2006.01) |
| ***A61L 17/10*** | (2006.01) |
| ***A61L 17/14*** | (2006.01) |

(52) U.S. Cl.
CPC ............. *A61L 17/145* (2013.01); *A61L 17/10* (2013.01); *A61L 2420/02* (2013.01)

(58) Field of Classification Search
CPC .......... A61L 27/34; A61L 31/14; A61B 17/04
See application file for complete search history.

(56) References Cited

U.S. PATENT DOCUMENTS

| | | | |
|---|---|---|---|
| 3,131,957 | A | 5/1964 | Musto |
| 3,752,516 | A | 8/1973 | Mumma |
| 4,403,797 | A | 9/1983 | Ragland, Jr. |
| 4,662,376 | A | 5/1987 | Belanger |
| 4,807,625 | A | 2/1989 | Singleton |
| 5,144,961 | A | 9/1992 | Chen et al. |
| 5,147,316 | A | 9/1992 | Castillenti |
| 5,312,423 | A | 5/1994 | Rosenbluth et al. |
| 5,391,176 | A | 2/1995 | de la Torre |
| 5,405,352 | A | 4/1995 | Weston |
| 5,454,821 | A | 10/1995 | Harm et al. |
| 5,472,446 | A | 12/1995 | de la Torre |

(Continued)

FOREIGN PATENT DOCUMENTS

| | | | |
|---|---|---|---|
| EP | 0791330 | A3 | 11/1997 |
| EP | 3505077 | A1 | 7/2019 |

(Continued)

OTHER PUBLICATIONS

Alfieri, 0. et al., "The double-orifice technique in mitral valve repair: a +A198:A225simple solution for complex problems," (2001) J. Thorne. Cardiovasc. Surg., 122(4):674-681.

(Continued)

*Primary Examiner* — Cachet I Proctor
(74) *Attorney, Agent, or Firm* — Chang & Hale LLP

(57) ABSTRACT

A method of preparing a suture for use in medical treatment involves treating a surface of the suture, applying a coating to the suture, and treating the coating to cause adhesion of the coating to the suture.

20 Claims, 7 Drawing Sheets

(56) References Cited

U.S. PATENT DOCUMENTS

| | | | | |
|---|---|---|---|---|
| 5,507,754 | A | 4/1996 | Green et al. | |
| 5,527,323 | A | 6/1996 | Jervis et al. | |
| 5,554,184 | A | 9/1996 | Machiraju | |
| 5,626,614 | A | 5/1997 | Hart | |
| 5,643,293 | A | 7/1997 | Kogasaka et al. | |
| 5,681,331 | A | 10/1997 | de la Torre et al. | |
| 5,716,368 | A | 2/1998 | de la Torre et al. | |
| 5,727,569 | A | 3/1998 | Benetti et al. | |
| 5,728,109 | A | 3/1998 | Schulze et al. | |
| 5,746,752 | A | 5/1998 | Burkhart | |
| 5,769,862 | A | 6/1998 | Kammerer et al. | |
| 5,797,928 | A | 8/1998 | Kogasaka | |
| 5,824,065 | A | 10/1998 | Gross | |
| 5,931,868 | A | 8/1999 | Gross | |
| 5,957,936 | A | 9/1999 | Yoon et al. | |
| 5,971,447 | A | 10/1999 | Steck, III | |
| 6,010,531 | A | 1/2000 | Donlon et al. | |
| 6,074,417 | A | 6/2000 | Peredo | |
| 6,269,819 | B1 | 8/2001 | Oz et al. | |
| 6,332,893 | B1 | 12/2001 | Mortier et al. | |
| 6,562,051 | B1 | 5/2003 | Bolduc et al. | |
| 6,626,930 | B1 | 9/2003 | Allen et al. | |
| 6,629,534 | B1 | 10/2003 | St. Goar et al. | |
| 6,752,810 | B1 | 6/2004 | Gao et al. | |
| 6,840,246 | B2 | 1/2005 | Downing | |
| 6,921,408 | B2 | 7/2005 | Sauer | |
| 6,940,246 | B2 | 9/2005 | Mochizuki et al. | |
| 6,978,176 | B2 | 12/2005 | Lattouf | |
| 6,991,635 | B2 | 1/2006 | Takamoto et al. | |
| 6,997,950 | B2 | 2/2006 | Chawla | |
| 7,112,207 | B2 | 9/2006 | Allen et al. | |
| 7,291,168 | B2 | 11/2007 | Macoviak et al. | |
| 7,294,148 | B2 | 11/2007 | McCarthy | |
| 7,306,729 | B2 * | 12/2007 | Bacino | B01D 67/0027 210/500.36 |
| 7,309,086 | B2 | 12/2007 | Carrier | |
| 7,316,706 | B2 | 1/2008 | Bloom et al. | |
| 7,373,207 | B2 | 5/2008 | Lattouf | |
| 7,431,692 | B2 | 10/2008 | Zollinger et al. | |
| 7,513,908 | B2 | 4/2009 | Lattouf | |
| 7,534,260 | B2 | 5/2009 | Lattouf | |
| 7,608,091 | B2 | 10/2009 | Goldfarb et al. | |
| 7,618,449 | B2 | 11/2009 | Tremulis et al. | |
| 7,632,308 | B2 | 12/2009 | Loulmet | |
| 7,635,386 | B1 | 12/2009 | Gammie | |
| 7,666,196 | B1 | 2/2010 | Miles | |
| 7,744,609 | B2 | 6/2010 | Allen et al. | |
| 7,837,727 | B2 | 11/2010 | Goetz et al. | |
| 7,871,368 | B2 | 1/2011 | Zollinger et al. | |
| 7,871,433 | B2 | 1/2011 | Lattouf | |
| 7,959,650 | B2 | 6/2011 | Kaiser et al. | |
| 8,029,518 | B2 | 10/2011 | Goldfarb et al. | |
| 8,029,565 | B2 | 10/2011 | Lattouf | |
| 8,043,368 | B2 | 10/2011 | Crabtree | |
| 8,147,542 | B2 | 4/2012 | Maisano et al. | |
| 8,187,323 | B2 | 5/2012 | Mortier et al. | |
| 8,226,711 | B2 | 7/2012 | Mortier et al. | |
| 8,241,304 | B2 | 8/2012 | Bachman | |
| 8,252,050 | B2 | 8/2012 | Maisano et al. | |
| 8,292,884 | B2 | 10/2012 | Levine et al. | |
| 8,303,622 | B2 | 11/2012 | Alkhatib | |
| 8,333,788 | B2 | 12/2012 | Maiorino | |
| 8,382,829 | B1 | 2/2013 | Call et al. | |
| 8,439,969 | B2 | 5/2013 | Gillinov et al. | |
| 8,454,656 | B2 | 6/2013 | Tuval | |
| 8,465,500 | B2 | 6/2013 | Speziali | |
| 8,475,525 | B2 | 7/2013 | Maisano et al. | |
| 8,500,800 | B2 | 8/2013 | Maisano et al. | |
| 8,608,758 | B2 | 12/2013 | Singhatat et al. | |
| 8,663,278 | B2 | 3/2014 | Mabuchi et al. | |
| 8,771,296 | B2 | 7/2014 | Nobles et al. | |
| 8,828,053 | B2 | 9/2014 | Sengun et al. | |
| 8,852,213 | B2 | 10/2014 | Gammie et al. | |
| 8,888,791 | B2 | 11/2014 | Jaramillo et al. | |
| 8,940,008 | B2 | 1/2015 | Kunis | |
| 9,131,884 | B2 | 9/2015 | Holmes et al. | |
| 9,192,287 | B2 | 11/2015 | Saadat et al. | |
| 10,076,414 | B2 | 9/2018 | Rourke et al. | |
| 2002/0013571 | A1 | 1/2002 | Goldfarb et al. | |
| 2003/0023254 | A1 | 1/2003 | Chiu | |
| 2003/0094180 | A1 | 5/2003 | Benetti | |
| 2003/0105519 | A1 | 6/2003 | Fasol et al. | |
| 2003/0120264 | A1 | 6/2003 | Lattouf | |
| 2003/0120341 | A1 | 6/2003 | Shennib et al. | |
| 2004/0044365 | A1 | 3/2004 | Bachman | |
| 2004/0093023 | A1 | 5/2004 | Allen et al. | |
| 2004/0199183 | A1 | 10/2004 | Oz et al. | |
| 2005/0004667 | A1 | 1/2005 | Swinford et al. | |
| 2005/0019735 | A1 | 1/2005 | Demas | |
| 2005/0075654 | A1 | 4/2005 | Kelleher | |
| 2005/0119735 | A1 | 6/2005 | Spence et al. | |
| 2005/0149067 | A1 | 7/2005 | Takemoto et al. | |
| 2005/0149093 | A1 | 7/2005 | Pokorney | |
| 2005/0154402 | A1 | 7/2005 | Sauer et al. | |
| 2005/0216036 | A1 | 9/2005 | Nakao | |
| 2005/0216077 | A1 | 9/2005 | Mathis et al. | |
| 2005/0261710 | A1 | 11/2005 | Sakamoto et al. | |
| 2005/0267493 | A1 | 12/2005 | Schreck et al. | |
| 2006/0030866 | A1 | 2/2006 | Schreck | |
| 2006/0100698 | A1 | 5/2006 | Lattouf | |
| 2006/0111739 | A1 | 5/2006 | Staufer et al. | |
| 2006/0167541 | A1 | 7/2006 | Lattouf | |
| 2006/0190030 | A1 | 8/2006 | To et al. | |
| 2006/0282088 | A1 | 12/2006 | Ryan | |
| 2007/0001857 | A1 | 1/2007 | Hartmann et al. | |
| 2007/0049952 | A1 | 3/2007 | Weiss | |
| 2007/0055292 | A1 | 3/2007 | Ortiz et al. | |
| 2007/0112422 | A1 | 5/2007 | Dehdashtian | |
| 2007/0112425 | A1 | 5/2007 | Schaller et al. | |
| 2007/0118151 | A1 | 5/2007 | Davidson | |
| 2007/0118154 | A1 | 5/2007 | Crabtree | |
| 2007/0149995 | A1 | 6/2007 | Quinn et al. | |
| 2007/0197858 | A1 | 8/2007 | Goldfarb et al. | |
| 2007/0213582 | A1 | 9/2007 | Zollinger et al. | |
| 2007/0270793 | A1 | 11/2007 | Lattouf | |
| 2008/0004597 | A1 | 1/2008 | Lattouf et al. | |
| 2008/0009888 | A1 | 1/2008 | Ewers et al. | |
| 2008/0065203 | A1 | 3/2008 | Khalapyan | |
| 2008/0140093 | A1 | 6/2008 | Stone et al. | |
| 2008/0167714 | A1 | 7/2008 | St. Goar et al. | |
| 2008/0188893 | A1 | 8/2008 | Selvitelli et al. | |
| 2008/0195126 | A1 | 8/2008 | Solem | |
| 2008/0228223 | A1 | 9/2008 | Alkhatib | |
| 2008/0249504 | A1 | 10/2008 | Lattouf et al. | |
| 2008/0269781 | A1 | 10/2008 | Funamura et al. | |
| 2009/0005863 | A1 | 1/2009 | Goetz et al. | |
| 2009/0043153 | A1 | 2/2009 | Zollinger et al. | |
| 2009/0105729 | A1 | 4/2009 | Zentgraf | |
| 2009/0105751 | A1 | 4/2009 | Zentgraf | |
| 2009/0276038 | A1 | 11/2009 | Tremulis et al. | |
| 2010/0023056 | A1 | 1/2010 | Johansson et al. | |
| 2010/0023117 | A1 | 1/2010 | Yoganathan et al. | |
| 2010/0023118 | A1 | 1/2010 | Medlock et al. | |
| 2010/0042147 | A1 | 2/2010 | Janovsky et al. | |
| 2010/0174297 | A1 | 7/2010 | Speziali | |
| 2010/0179574 | A1 | 7/2010 | Longoria et al. | |
| 2010/0210899 | A1 | 8/2010 | Schankereli | |
| 2010/0298930 | A1 | 11/2010 | Orlov | |
| 2011/0015476 | A1 | 1/2011 | Franco | |
| 2011/0022083 | A1 | 1/2011 | DiMatteo et al. | |
| 2011/0022084 | A1 | 1/2011 | Sengun et al. | |
| 2011/0028995 | A1 | 2/2011 | Miraki et al. | |
| 2011/0029071 | A1 | 2/2011 | Zlotnick et al. | |
| 2011/0060407 | A1 | 3/2011 | Ketai et al. | |
| 2011/0106106 | A1 | 5/2011 | Meier et al. | |
| 2011/0144743 | A1 | 6/2011 | Lattouf | |
| 2011/0264208 | A1 | 10/2011 | Duffy et al. | |
| 2011/0270278 | A1 | 11/2011 | Overes et al. | |
| 2011/0288637 | A1 | 11/2011 | De Marchena | |
| 2011/0307055 | A1 | 12/2011 | Goldfarb et al. | |
| 2012/0004669 | A1 | 1/2012 | Overes et al. | |
| 2012/0143215 | A1 | 6/2012 | Corrao et al. | |
| 2012/0150223 | A1 | 6/2012 | Manos et al. | |
| 2012/0179184 | A1 | 7/2012 | Orlov | |

(56) References Cited

U.S. PATENT DOCUMENTS

| | | | |
|---|---|---|---|
| 2012/0184971 | A1 | 7/2012 | Zentgraf et al. |
| 2012/0203072 | A1 | 8/2012 | Lattouf et al. |
| 2012/0226294 | A1 | 9/2012 | Tuval |
| 2012/0226349 | A1 | 9/2012 | Tuval et al. |
| 2013/0018459 | A1 | 1/2013 | Maisano et al. |
| 2013/0035757 | A1 | 2/2013 | Zentgraf et al. |
| 2013/0253641 | A1 | 9/2013 | Lattouf |
| 2013/0282059 | A1 | 10/2013 | Ketai et al. |
| 2013/0345749 | A1 | 12/2013 | Sullivan et al. |
| 2014/0031926 | A1 | 1/2014 | Kudlik et al. |
| 2014/0039607 | A1 | 2/2014 | Kovach |
| 2014/0067052 | A1 | 3/2014 | Chau et al. |
| 2014/0114404 | A1 | 4/2014 | Gammie et al. |
| 2014/0214152 | A1 | 7/2014 | Bielefeld |
| 2014/0243968 | A1 | 8/2014 | Padala |
| 2014/0364938 | A1 | 12/2014 | Longoria et al. |
| 2015/0032127 | A1 | 1/2015 | Gammie et al. |
| 2015/0045879 | A1 | 2/2015 | Longoria et al. |
| 2019/0175346 | A1 | 6/2019 | Schaffner et al. |
| 2020/0155315 | A1 | 5/2020 | Zhang et al. |

FOREIGN PATENT DOCUMENTS

| | | | | |
|---|---|---|---|---|
| GB | 944215 A | * 12/1963 | ............ A61L 17/14 |
| JP | 2013517110 A | 5/2013 | |
| WO | 2004037463 A1 | 5/2004 | |
| WO | 2006127509 A2 | 11/2006 | |
| WO | 2007100268 A2 | 9/2007 | |
| WO | 2007119057 A1 | 10/2007 | |
| WO | 2008013869 A2 | 1/2008 | |
| WO | 2008124110 A3 | 12/2008 | |
| WO | 2008143740 A3 | 2/2009 | |
| WO | 2006078694 A3 | 4/2009 | |
| WO | 2009081396 A2 | 7/2009 | |
| WO | 2010070649 A1 | 6/2010 | |
| WO | 2010105046 A1 | 9/2010 | |
| WO | 2012137208 A1 | 10/2012 | |
| WO | 2013003228 A1 | 1/2013 | |
| WO | 2014093861 A1 | 6/2014 | |
| WO | 2015020816 A1 | 2/2015 | |
| WO | 2016192481 A1 | 12/2016 | |
| WO | WO-2019126518 A1 | * 6/2019 | ........... A61L 17/145 |

OTHER PUBLICATIONS

Barbero-Marcial, M. et al., "Transxiphoid Approach Without Median Sternotomy for the Repair of Atrial Septa! Defects," (1998) Ann. Thorne. Surg., 65(3):771-774.

Braunberger, E. et al., "Very long-term results (more than 20 years) of valve repair with Carpentier's echniques in nonheumatic mitral valve insufficiency," (2001) Circulation, I 04:1-8-1-11.

Carpentier, Alain, "Cardiac valve surgery—the 'French coffec-tion'," The Journal of Thoracic and Cardiovascular Surgery, vol. 86, No. 3, Sep. 1983, 15 pages.

David, T. E. et al., "Mitral valve repair by replacement of chordae tendineae with polytetrafluoroethylene sutures," ( 1991) J. Thorne. Cardiovasc. Surg., 101 (3 ):495-50.

David, T. E. et al., "Replacement of chordae tendineae with Gore-Tex sutures: a ten-year experience," ( 1996) J. Heart Valve Dis., 5( 4 ):352-355.

Doty, D. B. et al., "Full-Spectrum Cardiac Surgery Through a Minimal Incision: Mini-Sternotomy (Lower Half) Technique," ( 1998) Ann. Thorne. Surg., 65(2):573-577.

Duran, C. M. G. et al., "Techniques for ensuring the correct length of new mitral chords," (2003) .I. Heart Valve Dis., 12(2):156-161.

Eishi, K. et al., "Long-term results of artificial chordae implantation in patients with mitral valve prolapse," (1997) J. Heal1 Valve Dis., 6(6):594-598.

Frater, R. W. M. ct al., "Chordal replacement in mitral valve repair," ( 1990) Circulation, 82(suppl. IV):IV-125-IV-130.

Frater, R. W. M., "Anatomical rules for the plastic repair of a diseased mitral valve," ( 1964) Thorax. 19:458-464.

Huber, C.H. et al., "Direct Access Valve Replacement (DAVR)—are we entering a new era in cardiac surgery?" (2006) European Journal ofCardio-thoracic Surgery, 29:380-385.

Hvass, U. et al., "Papillary Muscle Sling: A New Functional Approach to Mitra! Repair in Patients With Ischernic Left Ventricular Dysfunction and Functional Mitral Regurgitation," (2003) Ann. Thorne. Surg., 75:809-811.

Kasegawa, H. ct al., "Simple method for detennining proper length of allificial chordae in mitral valve repair," ( 1994) Ann. Thorne. Surg., 57(1 ):237-239.

Kobayashi, J. et al., "Ten-year experience of chordal replacement with expanded polytetrafluoroethylene in mitral valve repair," (2000) Circulation, J 02(19 Suppl 3):1ii-30-Jii-34.

Kunzelman, K. et al., "Replacement of mitral valve posterior chordae tenclincae with expanded polytetrafluorocthylcnc suture: a finite element study," (1996) J. Card. Surg., 11(2):136-145.

Langer, F. et al., "RING plus STRING: Papillary muscle repositioning as an adjunctive repair technique for ischemic mitral regurgitation," (2007) J. Thorne. Cardiovasc. Surg., 133( I): 247-249.

Maisano, F. et al., "The double-orifice technique as a standardized approach to treat mitral regurgitation due to severe rnyxomatous disease: surgical technique," (2000) European Journal of Cardio-thorncic Surgery, 17(3):201-205.

Merendino, K. A. et al., "The open con-ection of rheumatic mitral regurgitation and/or stenosis with special reference to regurgitation treated by posterornedial annuloplasty utilizing a pump-oxygenator," (1959) Annals of Surgery, 150(1 ):5-22.

Minatoya, K. et al., "Pathologic aspects of polytetrafluoroethylene sutures in human heart," ( 1996) Ann. Thorac. Surg., 61 (3 ):883-887.

Mohty, D. ct al., "Very long-term survival and durability ofmitral valve repair for mitral valve prolapse," (2001) Circulation, 104:1-1-1-7.

*Neochord, Inc.* v. *University of Maryland, Bal Tim Ore*, Case No. JPR2016-00208, Decision on Institution of Inter Faries Review, 37 CFR §42. I 08, Paper 6, Entered May 24, 2016, 28 pages.

*Neochord, Inc.* v. *University of Maryland, Baltimore*, Case No. IPR2016-00208, Declaration of Dr. Lishan Aklog, dated Nov. 17, 2015, 91 pages.

*Neochord, Inc.* v. *University of Maryland, Baltimore*, Case No. IPR2016-00208, Petition for inter ParlesReview of U.S. Pat. No. 7,635,386, dated Nov. 18, 2015, 65 pages.

Nigro, J. J. et al., "Neochordal repair of the posterior mitral leaflet," (2004) J. Thorne. Cardiovasc. Surg., 127(2):440-447.

Phillips, M. R. et al., "Repair of anterior leaflet mitral valve prolapse: chordal replacement versus chordal shrntening," (2000) Ann. Thorac. Surg., 69(1 ):25-29.

Russo, M. J. ct al. • "Transapical Approach for Mitral Valve Repair during Insertion of a Left Ventricular Assist Device," Hindawi Publishing Corporation, The Scientific World Journal, V olumc 2013, Article ID 925310, [ online], Retrieved from the internet: <URL: http://dx.doi.org/J 0.1155/2013/92531 O> Apr. 11, 2013, 4 pages.

Sarsam, M.A. I., "Simplified technique for determining the length of artificial cl1ordae in milral valve repair," (2002) Ann. Thorac. Surg., 73(5): 1659-1660.

Savage, E. B. et al., Use of mitral valve repair: analysis of contemporary United States experience reported to the society of thoracic surgeons national cardiac database, . . . (2003) Ann. Thorne. Surg., 75:820-825.

Speziali, G. et al., "Co!l'ection of Mitra! Valve Regurgitation by Off-Pump, Transapical Placement of Artificial Chordae Tendinae, Results of the European TACT Trial," AATS 93rd Annual Meeting 2013, www.aats.org, 26 pages.

Suematsu, Y. et al., "Three-dimensional echo-guided beating heaii surgery without cardiopulmonary bypass: Atrial septa! defect closure in a swine model," (2005) J. Thorne. Cardiovasc. Surg., 130: 1348-1357.

Von Oppell, U. 0. et al., "Chordal replacement for both minimally invasive and conventional mitral valve surgery using prcrncasurcd Gore-Tex loops," (2000) Ann. Thorne. Surg., 70(6):2166-2168.

Zussa, C. et al., Artificial rnitral valve chordae: experimental and clinical experience;• ( 1990) Ann. Thorne. Surg., 50(3):367-373.

(56) References Cited

OTHER PUBLICATIONS

Zussa, C. et al., "Seven-year experience with chordal replacement with expanded polytetrafluoroethylene in floppymitral valve," (1994)1. Thorac. Cardiovasc. Surg., 108(1):37-41.
Zussa, C. et al., "Surgical technique for artificial rnitral chordae implantation," ( 1991) Journal of Cardiac Surgery, 6(4):432-438.
Zussa, C., "Artificial chordae," (1995) J. Heart Valve Dis., 4(2):S249-S256.

* cited by examiner

SUTURE ENCAPSULATION PROCESSES AND SYSTEMS

RELATED APPLICATION

This application is a continuation of International Patent Application No. PCT/US2022/019617, filed Mar. 9, 2022, which claims the benefit of U.S. Patent Application No. 63/159,377, filed on Mar. 10, 2021, the entire disclosures all of which are incorporated by reference for all purposes.

BACKGROUND

Technical Field

The disclosure herein relates to cardiac treatments, and more particularly to fully and/or partially encapsulated sutures for use in cardiac treatments.

Description of Related Art

Certain medical and other procedures involve the use of sutures or other similar devices. For example, transcatheter mitral valve repair can involve use of sutures for chordal replacement of non-functioning valves.

SUMMARY

For purposes of summarizing the disclosure, certain aspects, advantages and novel features have been described herein. It is to be understood that not necessarily all such advantages may be achieved in accordance with any particular instance. Thus, the disclosed instances may be carried out in a manner that achieves or optimizes one advantage or group of advantages as taught herein without necessarily achieving other advantages as may be taught or suggested herein.

Some implementations of the present disclosure involve a method of preparing a suture for use in medical treatment. The method comprises treating a surface of the suture, applying a coating to the suture, and treating the coating to cause adhesion of the coating to the suture.

In some instances, the coating has a form of a ribbon. The method may further comprise expanding the coating during application of the coating to the suture.

The suture and/or the coating may be at least partially composed of different materials. In some instances, the coating is at least partially composed of polytetrafluoroethylene and the suture is not composed of polytetrafluoroethylene. Expanding the coating may involve modifying the coating to be at least partially composed of expanded polytetrafluoroethylene.

In some instances, treating the coating involves applying heat to the coating. The suture may have a polyfilament structure.

The coating may be configured to maintain adhesion to the suture during twisting of the suture. In some instances, the coating has a tubular form. Treating the coating may involve shrinking the coating.

Some implementations of the present disclosure relate to a device for supporting a heart valve. The device comprises a suture and a coating configured to be applied to surface of the suture. The suture and the coating are at least partially composed of different materials.

In some instances, the coating is at least partially composed of polytetrafluoroethylene and the suture is not composed of polytetrafluoroethylene.

The coating may be configured to be stretched during application to the surface of the suture. In some instances, stretching the coating may involve modifying the coating to be at least partially composed of expanded polytetrafluoroethylene.

In some instances, the suture may have a polyfilament structure. The coating may have a tubular form.

Some implementations of the present disclosure relate to a method comprising delivering a coated suture to a ventricle of a heart. The coated suture comprises a suture and a coating configured to be applied to a surface of the suture. The method further comprises attaching a first end of the coated suture to a valve of the heart, attaching a second end of the coated suture to a ventricle wall of the heart, and tensioning the coated suture to form an artificial chord for the valve.

In some instances, delivering the coated suture involves coiling the coated suture around a delivery needle. Attaching the first end of the coated suture to the valve of the heart may involve forming the first end of the coated suture into a knot.

BRIEF DESCRIPTION OF THE DRAWINGS

Various instances are depicted in the accompanying drawings for illustrative purposes and should in no way be interpreted as limiting the scope of the disclosure. In addition, various features of different disclosed instances can be combined to form additional instances, which are part of this disclosure. Throughout the drawings, reference numbers may be reused to indicate correspondence between reference elements. However, it should be understood that the use of similar reference numbers in connection with multiple drawings does not necessarily imply similarity between respective instances associated therewith. Furthermore, it should be understood that the features of the respective drawings are not necessarily drawn to scale, and the illustrated sizes thereof are presented for the purpose of illustration of inventive aspects thereof. Generally, certain of the illustrated features may be relatively smaller than as illustrated in some instances or configurations.

Figure 1:
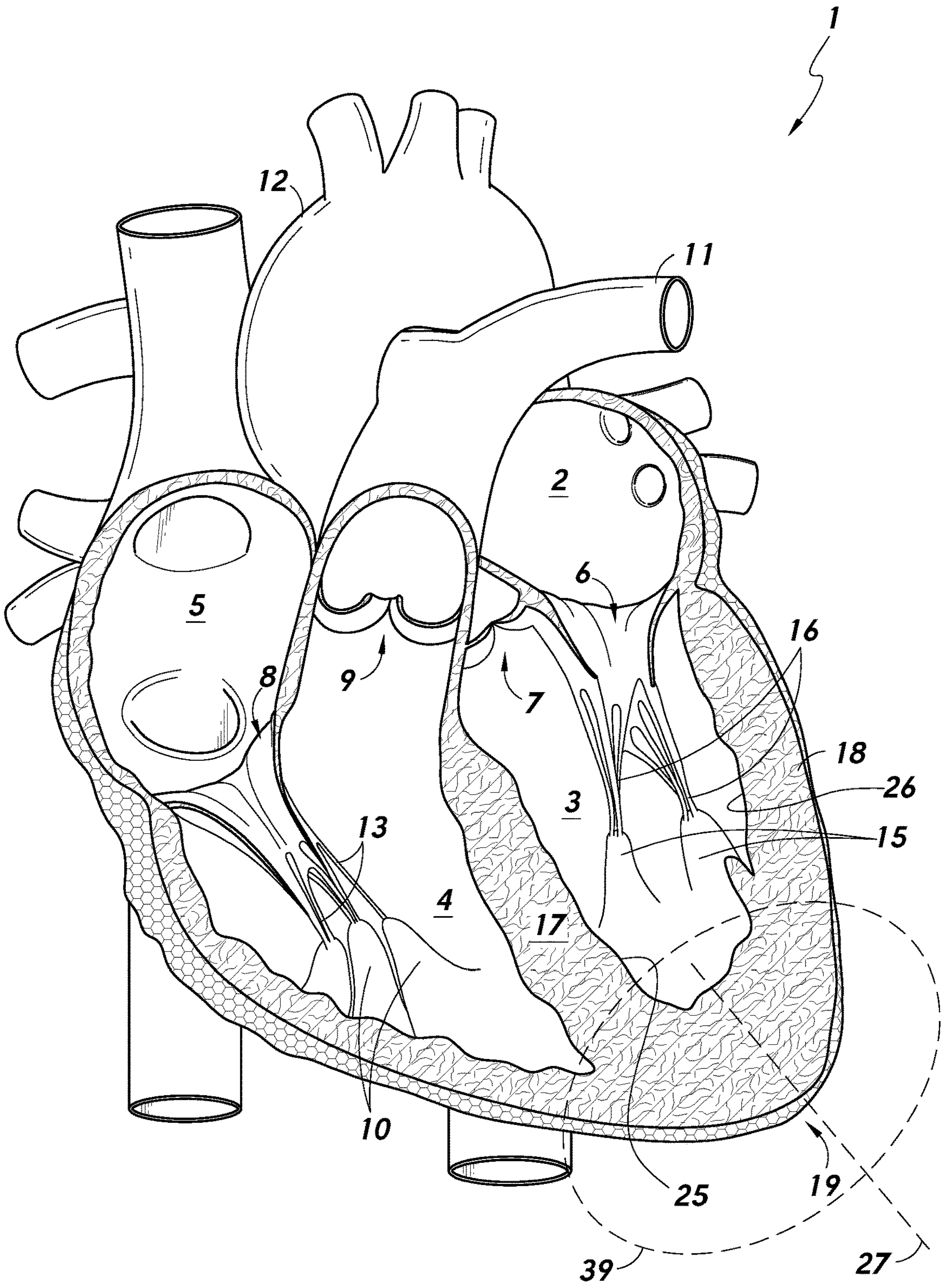
FIG. 1 is a cutaway view of the human heart.

To further clarify various aspects of instances of the present disclosure, a more particular description of certain instances will be made by reference to various aspects of the appended drawings. It is appreciated that these drawings depict only typical instances of the present disclosure and are therefore not to be considered limiting of the scope of the disclosure. Moreover, while the figures can be drawn to scale for some instances, the figures are not necessarily drawn to scale for all instances. Instances of the present disclosure will be described and explained with additional specificity and detail through the use of the accompanying drawings.

DETAILED DESCRIPTION

The headings provided herein are for convenience only and do not necessarily affect the scope or meaning of the disclosure or claims.

Although certain preferred instances and examples are disclosed below, inventive subject matter extends beyond the specifically disclosed instances to other alternative instances and/or uses and to modifications and equivalents thereof. Thus, the scope of the claims that may arise herefrom is not limited by any of the particular instances described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain instances; however, the order of description should not be construed to imply that these operations are order dependent. Additionally, the structures, systems, and/or devices described herein may be embodied as integrated components or as separate components. For purposes of comparing various instances, certain aspects and advantages of these instances are described. Not necessarily all such aspects or advantages are achieved by any particular instance. Thus, for example, various instances may be carried out in a manner that achieves or optimizes one advantage or group of advantages as taught herein without necessarily achieving other aspects or advantages as may also be taught or suggested herein.

The following description refers to the accompanying drawings, which illustrate specific instances. Other instances having different structures and operation do not depart from the scope of the disclosure.

Instances of the present disclosure provide solutions for sutures which may be used in treatment of certain structural heart conditions. Various disease processes can impair the proper functioning of one or more of the valves of the heart. These disease processes include degenerative processes (e.g., Barlow's disease, fibroelastic deficiency), inflammatory processes (e.g., rheumatic heart disease), and infectious processes (e.g., endocarditis). Additionally, damage to the ventricle from prior heart attacks (e.g., myocardial infarction secondary to coronary artery disease) or other heart diseases (e.g., cardiomyopathy) can distort the geometry of the heart causing valves in the heart to dysfunction. Many patients undergoing valve surgery, such as mitral valve surgery, suffer from a degenerative disease that causes a malfunction in a leaflet of the valve, which results in prolapse and regurgitation.

Valve regurgitation occurs when the leaflets of the valve do not close completely, thereby allowing blood to leak back into the prior chamber when the heart contracts. There are generally three mechanisms by which a valve becomes regurgitant or incompetent, including Carpentier's type I, type II and type III malfunctions. A Carpentier type I malfunction involves the dilation of the annulus such that the area of the valve orifice increases. The otherwise normally functioning leaflets do not have enough surface area to cover the enlarged orifice and fail to form a tight seal (e.g., do not coapt properly) causing regurgitation. Included in a type I mechanism malfunction are perforations of the valve leaflets, as in endocarditis. A Carpentier's type II malfunction involves prolapse of a segment of one or both leaflets above the plane of coaptation. This is the most commonly treated cause of mitral regurgitation, and is often caused by the stretching or rupturing of chordae tendineae (also referred to herein as "chords") normally connected to the leaflet. A Carpentier's type III malfunction involves restriction of the motion of one or more leaflets such that the leaflets are abnormally constrained below the level of the plane of the annulus. Leaflet restriction can be caused by rheumatic heart disease (IIIa) or dilation of the ventricle (IIIb).

Mitral valve disease is the most common valvular heart disorder, with nearly 4 million Americans estimated to have moderate to severe mitral valve regurgitation ("MR"), with similar numbers of individuals impacted outside of the United States. MR can result in a volume overload on the left ventricle which in turn progresses to ventricular dilation, decreased ejection performance, pulmonary hypertension, symptomatic congestive heart failure, atrial fibrillation, right ventricular dysfunction, and/or death. Successful surgical mitral valve repair can at least partially restore mitral valve competence, abolish the volume overload on the left ventricle, improve symptom status, and/or prevent adverse left ventricular remodeling. While generally safe and effective, conventional open-heart operations are invasive, result in significant disability, and require extended post-procedure recovery. Patients routinely spend five to seven days in the hospital and often are not able to return to normal daily activities for a month or more.

In many instances of mitral valve regurgitation, repair may be preferable to valve replacement. There are a variety of advantages to performing heart valve repair (e.g., mitral valve repair) using less invasive procedures while the heart is still beating, as described in detail herein. Mitral valve repair procedures may rely upon use of visualization technology, such as sonic guidance, which may have limitations that can reduce the effectiveness of such repairs. Accordingly, there is a continuing need for new procedures and devices for performing less invasive mitral valve repairs which do not require cardiac arrest and are less technologically challenging.

In some implementations, the present disclosure relates to an anchor delivery system configured to deliver one or more sutures into a heart. The term "suture" is used herein according to its plain and ordinary meaning and may refer to any elongate cord strip, cable, strand, line, tie, string, ribbon, strap, or portion thereof, or other type of material used in medical procedures. One having ordinary skill in the art will understand that a wire or other similar material may be used in place of a suture. Furthermore, in some contexts herein, the terms "cord" and "suture" may be used substantially interchangeably. In addition, use of the singular form of any of the suture-related terms listed above, including the terms "suture" and "cord," may be used to refer to a single suture/cord, or to a portion thereof. For example, where a suture knot or anchor is deployed on a distal side of a tissue portion, and where two suture portions extend from the knot/anchor on a proximal side of the tissue, either of the suture portions may be referred to as a "suture" or a "cord," regardless of whether both portions are part of a unitary suture or cord. A suture may be a means for tensioning and/or a means for anchoring that may be used in various medical procedures.

Some sutures may be at least partially composed of polytetrafluoroethylene (PTFE) and/or expanded PTFE (ePTFE). While ePTFE can have relatively high biostability, lubricity, and/or softness, over time ePTFE may be susceptible to creep, stretching, and/or fatigue. Accordingly, the effectiveness of ePTFE sutures can be diminished over time, particularly for ePTFE sutures used as artificial cords. Braided sutures can be at least partially resistant to creep and/or fatigue and/or may provide relatively good knot security but can cause more tissue inflammation and/or fibrous tissue encapsulation during healing than monofilament sutures. For example, a multi-filament/polyfilament suture can introduce potential for tissue growth and/or bacteria to develop between the filaments. Moreover, a braided suture can be abrasive to the tissue.

Suture materials (e.g., forming a suture and/or chord backbone) other than ePTFE can include absorbable synthetic materials, including: aliphatic polyesters; polyglycolic acid (PGA); poly(glycolide-co-L-lactide) copolymer (PGLA); poly-p-dioxanone (PDS); poly(glycolide-co-ε-caprolactone) copolymer; poly(glycolide-trimethylene carbonate-dioxanone) triblock copolymer; poly(glycolide-co-trimethylene carbonate-co-ε-caprolactone) copolymer; poly (glycolide-co-lactide-co-trimethylene carbonate-co-ε-caprolactone) copolymer or polyglytone 6211; polylactide (PLA); and polyhydroxyalkanoates (PHA). Suture materials can also include non-absorbable natural materials (e.g., silk) and/or synthetic materials, including: polyesters (PET); polyamides: nylon 66, nylon 6; polyolefins (polypropylene (PP), ultra-high molecular weight polyethylene (UHMWPE), brands names DYNEEMA® suture (Royal DSM) or FORCEFIBER® suture (Teleflex)); polytetrafluoroethylene (PTFE); polyvinylidene fluoride (PVDF); and/or metals (e.g., stainless steels and/or nitinols). Suitable suture materials can also include mixtures or composites of one or more suitable materials. Sutures formed of such materials can provide an improved overall long-term mechanical performance when compared to ePTFE sutures, though may have drawbacks including lower biostability, lubricity, and/or softness when compared to ePTFE sutures.

In some instances, a suture may be at least partially enclosed/encapsulated by a coating and/or ribbon. A "coating" and/or "means for coating" can include any material that may be configured to adhere to a surface of a suture and/or other device. The coating/ribbon may be at least partially composed of one or more materials different from one or more materials forming the suture. For example, a coating may be at least partially composed of a first material (e.g., ePTFE and/or PTFE) while a suture may not be composed of the first material. Such coated sutures may be ideal for use in various treatments including mitral valve repair due to their strength, handling ability, and/or ability to form secure knots. Coated sutures may be resistant to stretching, creep, and/or fatigue and/or may be configured to recoil to an original length with heart contraction. At least partially coating a suture can combine a mechanical robustness (e.g., creep resistance) of the suture (e.g., a braided suture) with a lubricity and/or inflammation resistance of a coating material (e.g., ePTFE). In some instances, a suture may have a polyfilament structure (e.g., in a braided form).

Certain inventive features disclosed herein relate to the delivery of suture knots associated with certain heart valve repair systems and devices, and/or systems, process, and devices for repairing any other type of target organ tissue. The term "associated with" is used herein according to its broad and ordinary meaning. For example, where a first feature, element, component, device, or member is described as being "associated with" a second feature, element, component, device, or member, such description should be understood as indicating that the first feature, element, component, device, or member is physically coupled, attached, or connected to, integrated with, or otherwise physically related to the second feature, element, component, device, or member.

The following includes a general description of human cardiac anatomy that is relevant to certain inventive features and instances disclosed herein and is included to provide context for certain aspects of the present disclosure. In humans and other vertebrate animals, the heart generally comprises a muscular organ having four pumping chambers, wherein the flow thereof is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aorta, etc.).

FIG. 1 illustrates an example representation of a heart 1 having various features relevant to certain aspects of the present inventive disclosure. The heart 1 includes four chambers, namely the left ventricle 3, the left atrium 2, the right ventricle 4, and the right atrium 5. A wall of muscle, referred to as the septum 17, separates the left 2 and right 5 atria and the left 3 and right 4 ventricles. The inferior tip 19 of the heart 1 is referred to as the "apex" 19 and is generally located on the midclavicular line, in the fifth intercostal space. The apex 19 can be considered part of the greater apical region 39.

The left ventricle 3 is the primary pumping chamber of the heart 1. A healthy left ventricle is generally conical and/or apical in shape in that it is longer (along a longitudinal axis extending in a direction from the aortic valve 7 to the apex 19) than it is wide (along a transverse axis extending between opposing walls 25, 26 at the widest point of the left ventricle) and descends from a base (including the left ventricle papillary muscles 15) with a decreasing cross-sectional circumference to the point or apex 19. Generally, the apical region 39 of the heart is a bottom region of the heart that is within the left or right ventricular region but is distal to the mitral 6 and tricuspid 8 valves and toward the tip of the heart. More specifically, the apical region 39 may be considered to be within about 20 cm to the right or to the left of the median axis 27 of the heart 1.

The pumping of blood from the left ventricle is accomplished by a squeezing motion and a twisting or torsional motion. The squeezing motion occurs between the lateral wall 18 of the left ventricle and the septum 17. The twisting motion is a result of heart muscle fibers that extend in a circular or spiral direction around the heart. When these fibers contract, they produce a gradient of angular displacements of the myocardium from the apex 19 to the base about the longitudinal axis of the heart. The resultant force vectors extend at angles from about 30-60 degrees to the flow of blood through the aortic valve 7. The contraction of the heart is manifested as a counterclockwise rotation of the apex 19 relative to the base, when viewed from the apex 19. A healthy heart can pump blood from the left ventricle in a very efficient manner due to the spiral contractility of the heart.

The heart 1 further includes four valves for aiding the circulation of blood therein, including the tricuspid valve 8, which separates the right atrium 5 from the right ventricle 4. The tricuspid valve 8 may generally have three cusps or leaflets and may generally close during ventricular contraction (e.g., systole) and open during ventricular expansion (e.g., diastole). The valves of the heart 1 further include the pulmonary valve 9, which separates the right ventricle 4 from the pulmonary artery 11 and may be configured to open during systole so that blood may be pumped toward the lungs, and close during diastole to prevent blood from leaking back into the heart from the pulmonary artery. The pulmonary valve 9 generally has three cusps/leaflets, wherein each one may have a crescent-type shape. The heart 1 further includes the mitral valve 6, which generally has two cusps/leaflets and separates the left atrium 2 from the left ventricle 3. The mitral valve 6 may generally be configured to open during diastole so that blood in the left atrium 2 can flow into the left ventricle 3, and advantageously close during diastole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

The atrioventricular (e.g., mitral and tricuspid) heart valves may comprise a collection of chordae tendineae (13, 16) and papillary muscles (10, 15) for securing the leaflets of the respective valves to promote and/or facilitate proper coaptation of the valve leaflets and prevent prolapse thereof. The papillary muscles, for example, may generally comprise finger-like projections from the ventricle wall. With respect to the tricuspid valve 8, the normal tricuspid valve may comprise three leaflets and three corresponding papillary muscles 10 (two shown in FIG. 1). The leaflets of the tricuspid valve may be referred to as the anterior, posterior and septal leaflets, respectively. The valve leaflets are connected to the papillary muscles 10 by the chordae tendineae 13, which are disposed in the right ventricle 4 along with the papillary muscles 10.

Surrounding the ventricles (3, 4) are a number of arteries (not shown) that supply oxygenated blood to the heart muscle and a number of veins that return the blood from the heart muscle. The coronary sinus (not shown) is a relatively large vein that extends generally around the upper portion of the left ventricle 3 and provides a return conduit for blood returning to the right atrium 5. The coronary sinus terminates at the coronary ostium (not shown) through which the blood enters the right atrium.

With respect to the mitral valve 6, a normal mitral valve may comprise two leaflets (anterior and posterior) and two corresponding papillary muscles 15. The papillary muscles 15 originate in the left ventricle wall and project into the left ventricle 3. Generally, the anterior leaflet may cover approximately two-thirds of the valve annulus. Although the anterior leaflet covers a greater portion of the annulus, the posterior leaflet may comprise a larger surface area in certain anatomies.

Various disease processes can impair the proper functioning of one or more of the valves of the heart. These disease processes include degenerative processes (e.g., Barlow's disease, fibroelastic deficiency), inflammatory processes (e.g., rheumatic heart disease) and infectious processes (e.g., endocarditis). Additionally, damage to the ventricle from prior heart attacks (e.g., myocardial infarction secondary to coronary artery disease) or other heart diseases (e.g., cardiomyopathy) can distort the valve's geometry causing it to dysfunction. However, the vast majority of patients undergoing valve surgery, such as mitral valve surgery, suffer from a degenerative disease that causes a malfunction in one or more leaflets of the valve which results in prolapse and regurgitation.

The mitral valve 6 and tricuspid valve 8 can be divided into three parts: an annulus, leaflets, and a sub-valvular apparatus. The sub-valvular apparatus can be considered to include the papillary muscles 10, 15 and the chordae tendineae 13, 16, which can elongate and/or rupture. If a valve is functioning properly, when closed, the free margins or edges of the leaflets come together and form a tight junction, the are of which, in the mitral valve, is known as the line, plane or area of coaptation. Normally functioning mitral and tricuspid valves open when the ventricles relax allowing blood from the atrium to fill the decompressed ventricle. When the ventricle contracts, the chordae tendineae advantageously properly tether or position the valve leaflets such that the increase in pressure within the ventricle causes the valve to close, thereby preventing blood from leaking into the atrium and assuring that substantially all of the blood leaving the ventricle is ejected through the aortic valve 7 or pulmonic valve 9 and into the arteries of the body. Accordingly, proper function of the valves depends on a complex interplay between the annulus, leaflets, and sub-valvular apparatus. Lesions in any of these components can cause the valve to dysfunction and thereby lead to valve regurgitation.

Generally, there are three mechanisms by which a heart valve becomes regurgitant or incompetent; they include Carpentier's type I, type II and type III malfunctions. A Carpentier type I malfunction involves the dilation of the annulus such that normally functioning leaflets are distracted from each other and fail to form a tight seal (e.g., do not coapt properly). Included in a type I mechanism malfunction are perforations of the valve leaflets, as in endocarditis. A Carpentier's type II malfunction involves prolapse of one or both leaflets above the plane of coaptation. This is the most common cause of mitral regurgitation and is often caused by the stretching or rupturing of chordae tendineae normally connected to the leaflet. A Carpentier's type III malfunction involves restriction of the motion of one or more leaflets such that the leaflets are abnormally constrained below the level of the plane of the annulus. Leaflet restriction can be caused by rheumatic disease (IIIa) or dilation of the ventricle (IIIb).

One or more chambers in the heart 1 may be accessed in accordance with certain heart valve-repair procedures and/or other interventions. Access into a chamber in the heart may be made at any suitable site of entry. In some implementations, access is made to a chamber of the heart, such as a target ventricle (e.g., left ventricle) associated with a diseased heart valve, through the apical region 39. For example, access into the left ventricle 3 (e.g., to perform a mitral valve repair) may be gained by making a relatively small incision at the apical region 39, close to (or slightly skewed toward the left of) the median axis 27 of the heart. Access into the right ventricle 4 (e.g., to perform a tricuspid valve repair) may be gained by making a small incision into the apical region 39, close to or slightly skewed toward the right of the median axis 27 of the heart. Accordingly, the ventricle can be accessed directly via the apex, or via an off-apex location that is in the apical region 39 but slightly removed from the tip/apex, such as via lateral ventricular wall, a region between the apex and the base of a papillary muscle, or even directly at the base of a papillary muscle. In some implementations, the incision made to access the appropriate ventricle of the heart is no longer than about 1 mm to about 5 cm, from 2.5 mm to about 2.5 cm, or from about 5 mm to about 1 cm in length. When a percutaneous approach is sought, no incision into the apex region of the heart may be made, but rather access into the apical region 39 may be gained by direct needle puncture, for instance by an 18-gauge needle, through which an appropriate repair instrument can be advanced.

Certain inventive features disclosed herein relate to certain heart valve repair systems and devices, and/or systems, process, and devices for repairing any other type of target organ tissue. In some implementations, a tissue anchor delivery device may be employed in repairing a mitral valve in patients suffering from degenerative mitral regurgitation or other condition. In some implementations, a transapical off-pump echo-guided repair procedure is implemented in which at least part (e.g., a shaft portion/assembly) of a valve repair system is inserted in the left ventricle and steered to the surface of the diseased portion of a target mitral valve leaflet and used to deploy/implant a tissue anchor in the target leaflet. The tissue anchor (e.g., sutureform formed into a bulky knot, T-fastener, grappling hook, spike, umbrella structure, pad, etc.) may advantageously be integrated or coupled with one or more artificial/synthetic chords serving a function similar to that of chordae tendineae. Such artificial chord(s) may comprise suture(s) and/or suture ends and/or tail portions associated with a knot-type tissue anchor and may comprise any suitable or desirable material, such as expanded polytetrafluoroethylene (ePTFE) or the like. In some instances, cords and/or anchors described herein may be at least partially composed of organic, polymer, metal, and/or composite materials and/or may be at least partially ceramic-based.

Figure 2:
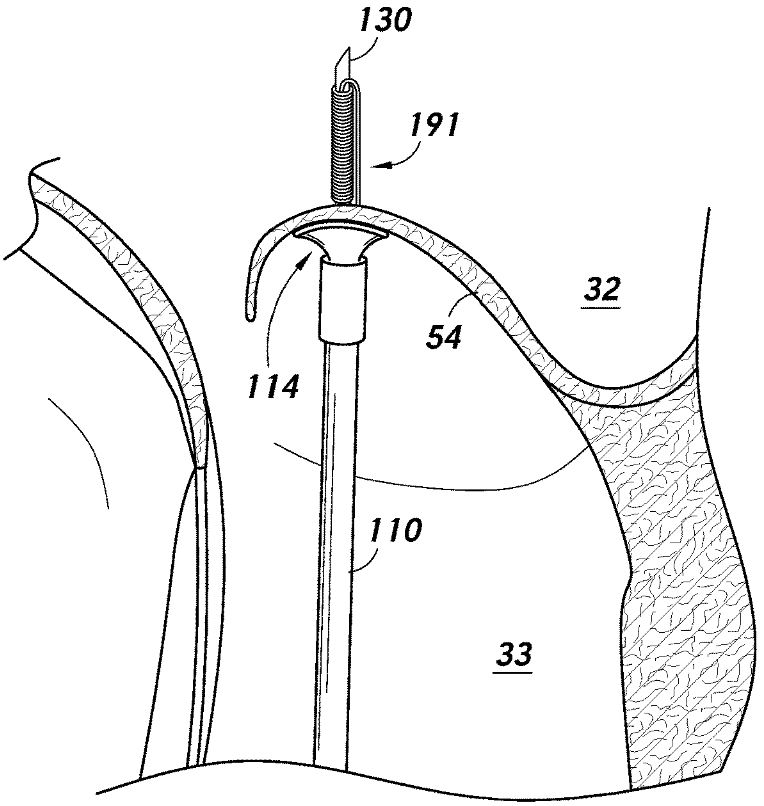
FIG. 2 is a perspective view of a tissue anchor delivery system in accordance with one or more examples.

FIG. 2 is a perspective view of a tissue anchor delivery system 100 in accordance with one or more instances. The tissue anchor delivery system 100 may be used to repair a heart valve, such as a mitral valve, and improve functionality thereof. For example, the tissue anchor delivery system 100 may be used to reduce the degree of mitral regurgitation in patients suffering from mitral regurgitation caused by, for example, midsegment prolapse of valve leaflets as a result of degenerative mitral valve disease. In order to repair such a valve, the tissue anchor delivery system 100 may be utilized to deliver and anchor tissue anchors, such as suture-knot-type tissue anchors, in a prolapsed valve leaflet. As described in detail below, such procedures may be implemented on a beating heart.

The delivery system 100 includes a rigid elongate tube no forming at least one internal working lumen. The term "lumen" is used herein according to its broad and ordinary meaning, and may refer to a physical structure forming a cavity, void, pathway, or other channel, such as an at least partially rigid elongate tubular structure, or may refer to a cavity, void, pathway, or other channel, itself, that occupies a space within an elongate structure (e.g., a tubular structure). Therefore, with respect to an elongate tubular structure, such as a shaft, tube, or the like, the term "lumen" may refer to the elongate tubular structure and/or to the channel or space within the elongate tubular structure. Although described in certain instances and/or contexts as comprising a rigid elongate tube, it should be understood that tubes, shafts, lumens, conduits, and the like disclosed herein may be either rigid, at least partially rigid, flexible, and/or at least partially flexible. Therefore, any such component described herein, whether or not referred to as rigid herein should be interpreted as possibly being at least partially flexible. In accordance with the present disclosure, the rigid elongate tube 110 may be referred to as a "shaft" for simplicity. Implementation of a valve-repair procedure utilizing the delivery system 100 can be performed in conjunction with certain imaging technology designed to provide visibility of the shaft 110 of the delivery system 100 according to a certain imaging modality, such as echo imaging. Generally, when performing a valve-repair procedure utilizing the tissue anchor delivery system 100, the operating physician may advantageously work in concert with an imaging technician, who may coordinate with the physician to facilitate successful execution of the valve-repair procedure.

The one or more lumens of the shaft **11*o* may be configured to house one or more needles (not shown) that may be configured to be wrapped at least in part with one or more pre-formed knot sutureform anchors, as described in detail herein. In some instances, the shaft 110 may be configured to form a relatively low profile. For example, the shaft 110 may have a diameter of approximately 0.5 inches or less. The shaft 110 may be associated with an atraumatic tip 114 feature. The atraumatic tip 114 can be an echogenic leaflet-positioner component, which may be used for deployment and/or positioning of the suture-type tissue anchor. In some instances, the tip 114 may be cone-shaped and/or may have any other shape. The atraumatic tip 114, disposed at the distal end of the shaft 11*o***, may be configured to have deployed therefrom one or more wrapped pre-formed suture knots (e.g., sutureforms), as described herein.

The atraumatic tip 114 may be referred to as an "end effector." In addition to one or more pre-formed knot sutureforms and/or associated needles, the shaft **11*o* may be configured to house one or more elongated knot pusher tubes (not shown; also referred to herein as "pushers"), which may be actuated simultaneously or sequentially using a plunger in some instances. As described in further detail below, the tip 114** can provide a surface against which the target valve leaflet may be held in connection with deployment of a leaflet anchor.

The delivery device 100 may be used to deliver one or more tissue anchors, as described in greater detail below. For example, the delivery device 100 may be utilized to deliver one or more tissue anchors (e.g., bulky knots) on a distal side of a mitral valve leaflet. While some instances described herein may refer to and/or describe "bulky knot" type tissue anchors, the delivery systems described herein may be configured for delivery of any of a variety of anchor types, including T-fasteners, hooks (e.g., grappling hooks), spikes, umbrella- and/or disc-shaped structures, and/or pads. The tip 114 (e.g., end effector), can be placed in contact with the ventricular side of a leaflet of a mitral valve 54.

One or more needles may have a pre-formed knot disposed about a distal portion thereof while maintained in the shaft 110. For example, a pre-formed knot may be formed of one or more sutures configured in a coiled sutureform having a plurality of winds/turns around a needle over a portion of the needle that may be associated with a longitudinal slot in the needle that can run from the distal end thereof. Although the term "sutureform" is used herein, it should be understood that such components/forms may comprise suture, wire, and/or any other elongate material wrapped or formed in a desired configuration. The coiled sutureform can be provided or shipped disposed around the needle The shaft 110 of the tissue anchor delivery device 100 may be inserted into a ventricle 33 (e.g., left ventricle) and approximated to a target valve leaflet 54 in connection with a valve-repair procedure in accordance with one or more instances of the present disclosure. For example, the valve leaflet 54 may be part of a mitral valve. The anchor delivery device shaft 110 can be configured to deliver a tissue anchor, such as a bulky knot to the valve leaflet 54. As an example, FIG. 2 shows a valve leaflet 54, which may represent a posterolateral leaflet of a mitral valve. It will be understood that the anchor delivery device shaft 110 can also or alternatively deliver a tissue anchor to the anteromedial mitral valve leaflet. Although the description of FIGS. 2-4 below is presented in the context of a mitral valve, it should be understood that the principles disclosed herein are applicable to other valves or biological tissues, such as a tricuspid valve.

Figure 3:
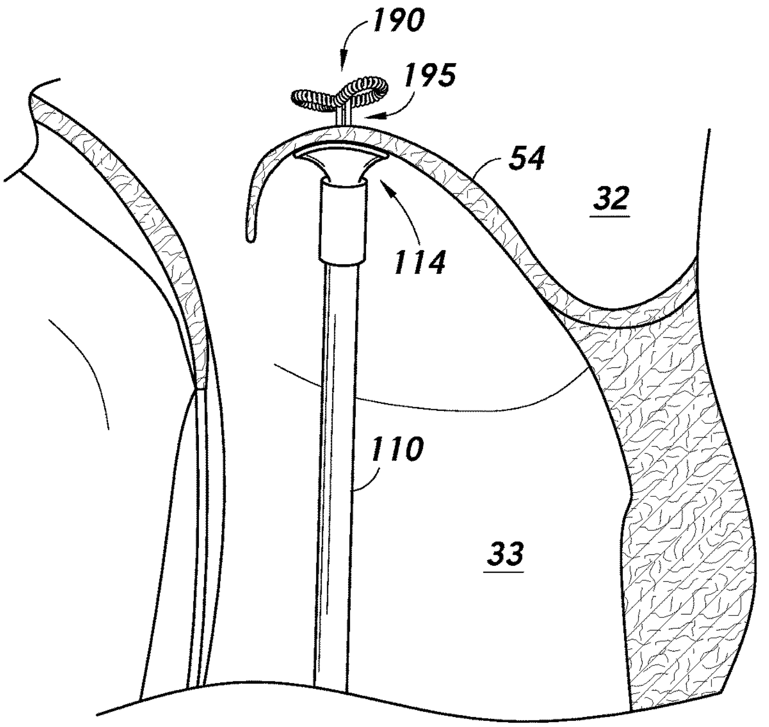
FIG. 3 provides a close-up view of the formed suture anchor on the atrial side of the leaflet in accordance with one or more examples.
Figure 4:
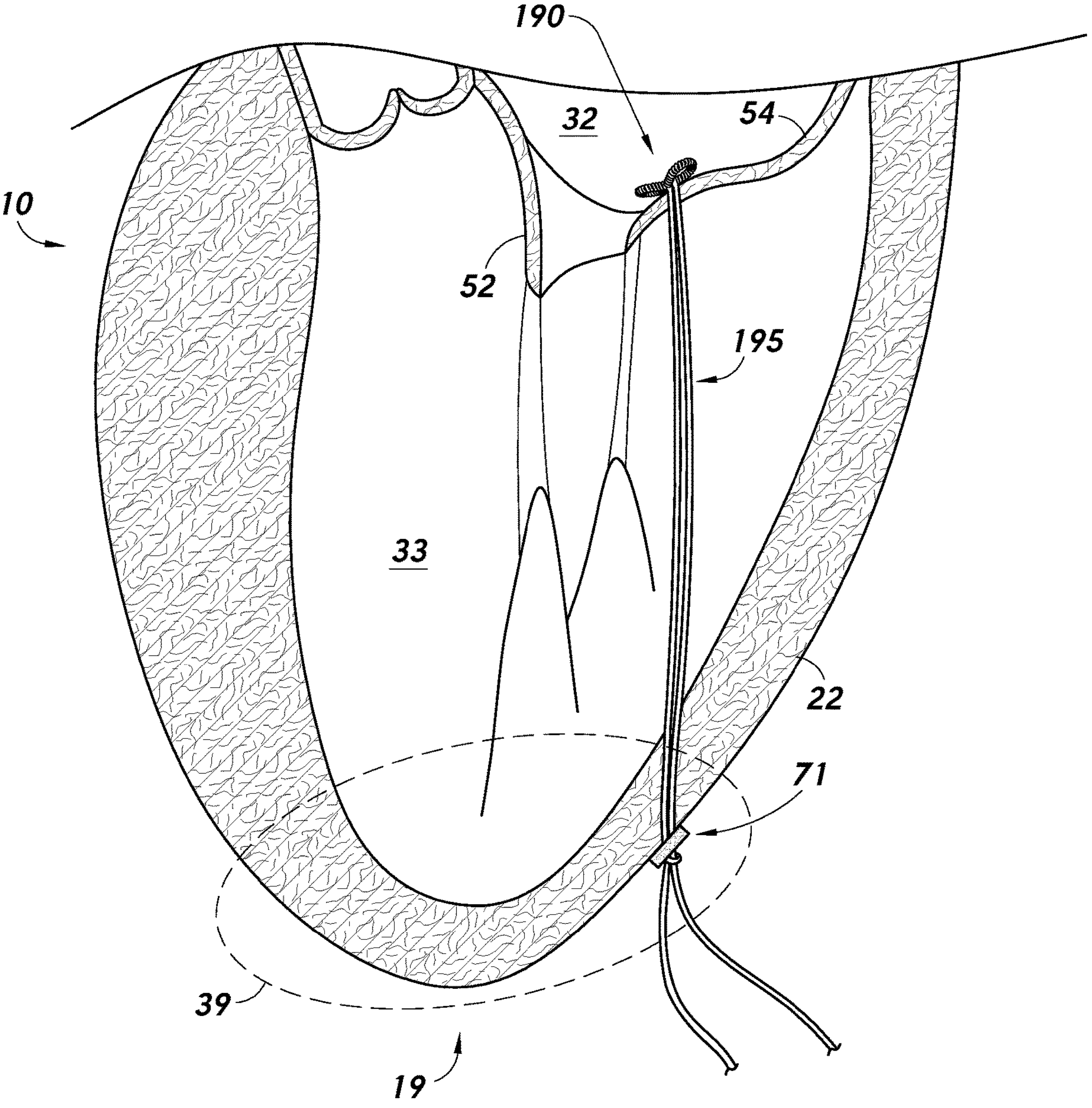
FIG. 4 shows a cutaway view of a deployed leaflet anchor in accordance with one or more examples.

With reference to FIGS. 2-4, the anchor delivery device shaft 110 can comprise one or more elongate lumens configured to allow delivery of one or more anchors to the valve leaflet 54. The shaft 110 can be configured to facilitate performance of one or more functions, such as grasping, suctioning, irrigating, cutting, suturing, or otherwise engaging a valve leaflet. The distal end, or tip, 114 of the shaft 110 can be configured to contact the mitral valve leaflet 54 without substantially damaging the leaflet to facilitate repair of the valve 36. For example, during a valve-repair procedure, a handle coupled to the shaft 110 can be manipulated in such a manner so that the leaflet 54 is contacted with the functional distal portion of the shaft 110 and a repair effectuated.

Echo imaging guidance, such as transesophageal echocardiogram (TEE) (2D and/or 3D), transthoracic echocardiogram (TTE), and/or intracardiac echo (ICE), may be used to assist in the advancement and desired positioning of the anchor delivery device shaft 110 within the ventricle 33. The distal end 114 of the shaft **11*o* can contact a proximal surface (e.g., underside surface with respect to the illustrated orientation of FIGS. 3 and 6-9) of the mitral valve leaflet 54, without or substantially without damaging the leaflet 54. For example, the end/tip portion or component 114 can have a relatively blunt form or configuration. The end/tip portion or component 114 can be configured to maintain contact with the proximal side of the valve leaflet 54 as the heart beats to facilitate reliable delivery of the anchor 191/190 to the target site on the leaflet 54**.

In some instances, one or more perforation devices (e.g., needle(s)) can be delivered through one or more working lumens (not shown) of the shaft 110 to the valve leaflet 54 to puncture the valve leaflet 54 and project one or more sutureforms 191 including a plurality of winds of suture about a distal portion of a needle 130 into the atrium 32, wherein the one or more sutureforms are deployed to form one or more bulky knot tissue anchor 190 (shown, e.g., in FIGS. 3 and 4). The sutureform 191 may represent a form of delivery of a suture. For example, delivering a suture into a heart may involve coiling the suture around a needle 130 to form a sutureform 191.

FIG. 2 shows the shaft 110 of the tissue anchor delivery device 100 positioned on the target valve leaflet 54 (e.g., mitral valve leaflet). For example, the target site of the valve 54 may be slowly approached from the ventricle side thereof by advancing the distal end of the shaft 110 along or near to the posterior wall of the ventricle 33 (e.g., left ventricle) without contacting the ventricle wall. Successful targeting and contacting of the target location on the leaflet 54 can depend at least in part on accurate visualization of the shaft 110 and/or tip/end effector 114 throughout the process of advancing the tip 114 to the target site. Generally, echocardiographic equipment may be used to provide the necessary or desired intra-operative visualization of the shaft 110 and/or tip 114.

Once the tip 114 is positioned in the desired position, the distal end of the shaft 110 and the tip 114 may be used to drape, or "tent," the leaflet 54 to better secure the tip 114 in the desired position, as shown in FIG. 2. Draping/tenting may advantageously facilitate contact of the tip 114 with the leaflet 54 throughout one or more cardiac cycles, to thereby provide more secure or proper deployment of leaflet anchor(s). The target location may advantageously be located relatively close to the free edge of the target leaflet 54 to minimize the likelihood of undesirable intra-atrial wall deployment of the anchor. Navigation of the tip 114 to the desired location on the underside of the target valve leaflet 54 may be assisted using echo imaging, as described in detail herein. Echo imaging may be relied upon to confirm correct positioning of the tip 114 prior to anchor/knot deployment.

With the shaft 110 positioned against the target leaflet 54, the plunger of the tissue anchor delivery device 100 can be actuated to move the one or more needles 130 and/or one or more pushers disposed within the shaft 110, such that the coiled sutureform portions 191 of the suture anchors slide off the needles 130. As the plunger is actuated, distal piercing portions of the needles 130 puncture the leaflet 54 and form one or more openings in the leaflet. A needle 130 and/or tissue anchor sutureform 191 may be projected therefrom through the target leaflet 54 in accordance with one or more instances. In some instances, a needle 130 may be configured to be projected a distance of between about 0.2-0.3 inches, or less, distally beyond the distal end of the shaft 110 (e.g., beyond the tip 114). In some instances, a needle 130 may be projected a distance of between about 0.15-0.4 inches. In some instances, a needle 130 may be projected a distance of about 1.0 inch, or greater. In some instances, a needle 130 may be configured to extend until a distal tip of the needle (e.g., a pointed tip) and/or the entire coiled sutureform 191 extend through the leaflet 54. The needle 130 and/or the distal tip of the needle may be configured to pierce and/or penetrate a leaflet of a heart valve. While one or more needles 130 and/or sutureforms 191 may be projected into the atrial side 32 of the leaflet 54, the shaft 110 and/or tip 114 may be advantageously configured to remain entirely on the ventricular side 33 of the leaflet 54. In some instances, one or more needles 130 may be configured to extend a greater distance from the shaft 110 than one or more other needles. For example, a first needle may be longer than a second needle. In another example, a first needle may be situated further along in the shaft 110 than a second needle. In another example, a first needle may be deployed before a second needle. In these examples, the second needle may be situated at least partially within the shaft 110 while the first needle pierces and/or passes through the leaflet 54.

As one or more pushers (not shown) within the tissue anchor delivery device shaft 110 are moved distally, distal ends of the pushers may advantageously move and/or push the distal coiled sutureforms 191 (e.g., pre-deployment coiled portions of the suture anchors) over the distal ends of the needles 130 and further within the atrium 32 of the heart on a distal side of the leaflet 54, such that the sutureforms extend distally beyond distal ends of the needles 130. For example, in some instances, at least half a length of a sutureform 191 may be configured to extend beyond the distal end of a needle 130. The pushers may be configured to press against the sutureforms 191 and/or the needles 130 may be configured to press the sutureforms 191 against the pushers. In some instances, at least three quarters of the length of a sutureform 191 may extend beyond the distal end of a needle 130. In some instances, an entire coiled sutureform 191 may be configured to extend beyond a distal end of a needle 130.

FIG. 3 provides a close-up view of the formed suture anchor 190 on the atrial side 32 of the leaflet 54. As shown in FIG. 3, after a sutureform 191 has been pushed off and/or removed from a needle 130, pulling one or more of the suture tail(s) 195 (e.g., suture strands extending from the coiled portion of the suture) associated with the tissue anchor 190 proximally can cause the sutureform 191 to form a bulky knot anchor 190. For example, the bulky knot suture anchor 190 may be formed by approximating opposite ends of the coils of the sutureform 191 towards each other to form one or more loops. After the sutureform 191 has been formed into the bulky knot 190, the delivery device 100 can be withdrawn proximally, leaving the tissue anchor 190 disposed on the distal atrial side of the leaflet 54. In some instances, two suture tails 195 for each bulky knot 190 may extend from the proximal/ventricle side 33 of the leaflet 54 and out of the heart 1. For example, the delivery device shaft 110 can be slid/withdrawn over the suture tail(s) 195. The bulky knot suture anchor 190 may represent a method of attaching a suture to the valve leaflet 54. For example, forming a suture into a bulky knot can cause attachment of the suture to the leaflet 54 due at least in part to the shape of the bulky knot preventing the suture from detaching from the leaflet 54 (e.g., passing through a hole in the leaflet 54).

FIG. 4 shows a cutaway view of a deployed leaflet anchor 190 in accordance with one or more instances of the present disclosure. While FIG. 4 shows one deployed leaflet anchor 190, any number of leaflet anchors may be deployed. The suture tails 195 coupled to the anchor 190 may be secured at the desired tension using a pledget 71 or other suture-fixing/locking device or mechanism on the outside of the heart through which the suture tails 195 may run. The knot 75 and/or other suture fixation mechanism or device may be implemented to hold the sutures at the desired tension and to the pledget 71. With the suture tail(s) 195 fixed to the ventricle wall 22, a ventricular portion of the suture tail(s) 195 (e.g., the portion of the suture tail 195 that is within the ventricle 33) may advantageously function as replacement leaflet chords (e.g., chordae tendineae) that may be configured to tether the target leaflet 54 in a desired manner.

In certain instances, the pledget 71 may be a low-porosity and/or relatively stiff pledget. Such a pledget may advantageously allow for the desired tension of the suture tails 195 to be sustained over an extended post-operative period of time. In some instances, suture tying and/or fixation may be implemented using one or more soft tissue retractors and/or right-angle clamps, which may have rubber shods associated therewith to reduce the risk of damage to the replacement chords.

In certain implementations, testing of location and/or tension of the anchor 190 and/or suture tail(s) 195 may be performed by gently tensioning the suture tails until leaflet motion is felt and/or observed. Echo imaging technology may be used to view and verify the anchor placement and resulting leaflet function. The steps and processes outlined above for placing one or more suture-knot-type tissue anchors may be repeated as necessary until the desired number of anchors have been implanted on the target valve leaflet. In some implementations, tension adjustment in the suture tail(s)/cord(s) associated with multiple leaflet anchors may be performed simultaneously. The appropriate number of leaflet anchors may advantageously be determined to produce the desired coaptation of the target valve leaflets 54, 52. All deployed leaflet anchors may advantageously be below the surface of coaptation. With respect to posterior mitral valve leaflet repair, the anterior leaflet may advantageously touch the posterior leaflet basal to the leaflet anchor(s). The pledget 71 may be drawn against the epicardial surface, and all the suture tails/cords 195 may be inserted through a tourniquet so that all chords can be tension to the desired effective coaptation together.

In some implementations, one or more leaflet anchors may be deployed in each of the mitral valve leaflets, and/or sutures/cords coupled to separate leaflets may be secured together in the heart by tying them together with knots and/or by another suitable attachment device, creating an edge-to-edge repair to decrease the septal-lateral distance of the mitral valve orifice.

With further reference to FIGS. 2-4, generally, the shaft 110 of the tissue anchor delivery device 100 may be slowly advanced into an introducer until the tip 114 has flushed the introducer and entered the ventricle 33. In so doing, it may be desirable to advance the shaft 110 within the ventricle 33 in such a way as to avoid traversing areas populated by papillary muscles and/or associated chordae tendineae to avoid entanglement therewith. In order to facilitate or ensure avoidance of such anatomy, imaging technology may advantageously be implemented to provide at least partial visibility of the shaft 110 within the ventricle 33, as well as certain anatomical features within the ventricle. With respect to visibility of the shaft 110 in the ventricle 33, echogenic characteristics of the shaft 110 can affect the visibility thereof using echo imaging modalities. Therefore, a shaft 110 having relatively high echogenicity as described in detail herein may advantageously allow for more accurate and/or simplified advancement of the shaft 110, as well as placement of the tip 114 at the target implantation site at the valve leaflet 54 (e.g., an anterior or posterior leaflet of a mitral valve). In some implementations, hybrid imaging technologies may be used, wherein echo imaging is used in combination with a different imaging modality. Multi-imaging modalities may provide improved visibility of anatomical and/or delivery system components.

Figure 5A:
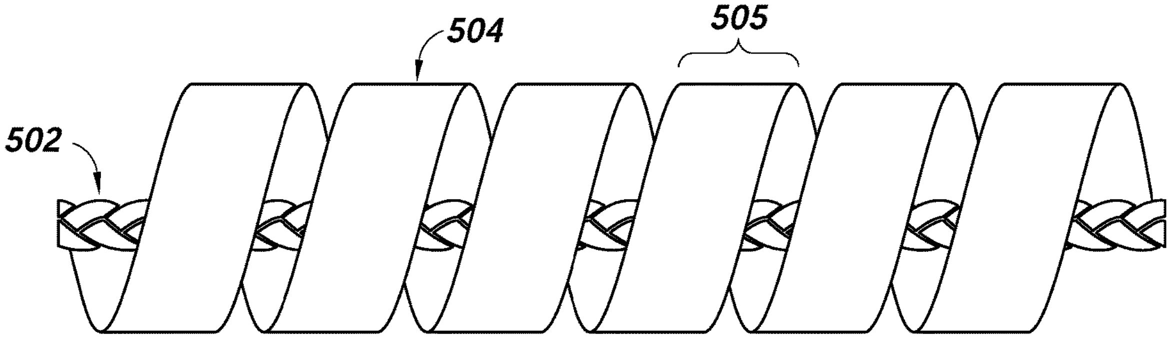
FIGS. 5A and 5B illustrate steps of a suture coating process in which a ribbon may be applied to an outer surface of a suture in accordance with some instances.
Figure 5B:
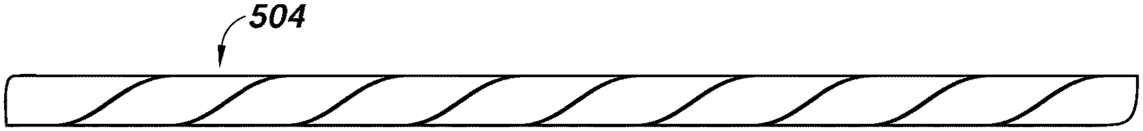

FIGS. 5A and 5B illustrate steps of a suture coating/encapsulation process in which a coating in the form of a ribbon 504 may be applied to an outer surface of a suture 502 to form a device for use in various medical treatments and/or procedures in accordance with some instances. Sutures 502 used in various treatments, including mitral valve repair, may be coated to improve lubricity, tissue overgrowth prevention, softness, biostability, and/or other features of the suture. A suture 502 may have a polyfilament structure and/or may comprise multiple filaments and/or strands twisted and/or braided together to provide relatively high tensile strength, pliability, and/or flexibility, among other things. However, while some coated sutures 502 described herein may comprise multiple filaments, coatings may be applied to monofilament sutures 502 to improve various features of the monofilament sutures. In some instances, a suture 502 may be composed at least partially of metal (e.g., nitinol, stainless steel, and/or cobalt chromium) and/or may comprise braided and/or twisted cables. Sutures 502 may have any of a variety of diameters and/or other specifications (e.g., as defined by the United States Pharmacopeia (USP), other pharmacopeia, or other standard).

A suture 502 may additionally or alternatively be at least partially composed of braided and/or twisted monofilament and/or polyfilament synthetic polymers. In some instances, suitable biostable synthetic polymers for use in sutures may include polyester, polypropylene (PP), polyamide 6 (PA6), polyethylene (PE), polysulfone (PSU), polyether ether ketone (PEEK), polyvinylidene fluoride (PVDF), high density and/or high molecular weight polyethylene (HDPE and/or HMWPE), ultra-high molecular weight polyethylene (UHMWPE), thermoplastic polyurethanes, polysiloxanes and/or polycarbonate-based polyurethanes, and/or synthetic fluoropolymers of tetrafluoroethylene (e.g., PTFE). A suture 502 may additionally or alternatively be at least partially composed of various bioresorbable suture materials including polylactide (PLA), polyglycolide (PGA), poly(ε-caprolactone) (PCL), poly(lactide-co-glycolide) (PLGA), poly (lactide-co-ε-caprolactone) (PLCL), silk, collagen, nylon, aliphatic, hydrophilic polyether-based thermoplastic polyurethanes (TPUs), and/or polyether block amide (e.g., PEBAX® elastomer, Arkema).

In some instances, at least a portion of an outer surface of the suture 502 may be treated prior to encapsulation by a coating including one or more coating materials and/or ribbons 504. While the coating is shown in FIGS. 5A and 5B as having a form of a ribbon 504, the coating may have other forms, including a tubular form (see, e.g., FIGS. 6A and 6B). In some instances, treatment of the outer surface of the suture 502 may involve activation of a surface chemistry of the suture 502. For example, suture surface activation can involve modifying the surface of the suture 502 using plasma and/or corona activation, discharge, and/or functionalization, which may be compatible with various chemicals including at least oxygen, argon, hydrogen, nitrogen, $CF_4$, and/or $SF_6$ plasma. In some instances, treating the outer surface of the suture 502 may be configured to improve adhesion of the ribbon 504 to the suture 502.

Surface activation of the suture 502 may be additionally or alternatively performed via chemical cleaning using, for example, organic solvents including isopropyl alcohol, toluene, acetone, ethanol, and/or hexane, among others. Additionally or alternatively, surface activation of the suture 502 may be performed, at least in part, using a suture hydrolyzation process involving use of acetic acid and/or hydrogen peroxide.

The ribbon 504 may be at least partially composed of any of a variety of materials. Suitable materials can include various biostable synthetic polymers, including PET, PP, PA6, PE, PSU, PEEK, PVDF, HDPE, HMWPE, UHMWPE, thermoplastic polyurethanes, polysiloxanes and/or polycarbonate-based polyurethanes, synthetic fluoropolymer of tetrafluoroethylene (e.g., PTFE), ePTFE, and/or perfluoroalkoxy alkane (PFA), among others. In some instances, the ribbon 504 may be at least partially composed of bioresorbable materials including PLA, PGA, PCL, PLGA, PLCL, silk, collagen, nylon, aliphatic, hydrophilic polyether-based TPUs, and/or polyether block amide, among others.

As shown in FIG. 5A, the ribbon 504 may have a generally flat structure to allow the ribbon 504 to lay flatly against a surface of the suture 502 without substantially increasing a width and/or diameter of the suture 502. The ribbon 504 may have any width 505 and/or may be wrapped around the suture 502 with any number of windings such that the ribbon 504 may cover at least a portion of the outer surface of the suture 502. In some instances, the ribbon 504 may be configured to cover an entire surface of the suture 502 and/or a continuous portion of the suture 502. For example, there may be no gaps between at least some windings of the ribbon 504 such that at least a portion of the suture 502 may be entirely encapsulated by the ribbon 504, as shown in FIG. 5B.

In some instances, the ribbon 504 may be configured to adhere to the suture 502 and/or to itself. For example, if the ribbon 504 overlaps with itself, the ribbon 504 may be configured to create a mechanical and/or chemical bonding with itself. In some instances, encapsulating the suture 502 may involve allowing for overlap of the ribbon 504 for at least some of the windings of the ribbon 504 to maximize bonding of the ribbon 504 around the suture 502. Additionally or alternatively, multiple layers of ribbons 504 may be applied to the suture 502 to ensure full encapsulation of at least a portion of the suture 502 and/or to improve mechanical and/or chemical bonding of the ribbons 504 around the suture 502.

The suture 502 may have a braided structure and/or may otherwise provide a relatively high surface area to maximize mechanical attachment to the ribbon 504. For example, the suture 502 may be composed of multiple braided and/or twisted filaments, each of which may be configured to adhere to and/or otherwise form an attachment with the ribbon 504.

In some instances, the ribbon 504 may be formed at least partially using compression molding of a powder (e.g., a polymer fine powder). The ribbon 504 may additionally or alternatively be extruded by passing a film (e.g., a polymer film) by a plurality of opposing calendar rolls to form a thin ribbon 504. The ribbon 504 may have any thickness, for example ranging from 15 μm to approximately 500 μm. The ribbon 504 may be formed at least partially through extrusion of a resin paste (e.g., a PTFE resin paste).

The ribbon 504 may be stretched and/or expanded (e.g., to form ePTFE from a PTFE ribbon 504) before and/or during an encapsulation process. For example, the ribbon 504 may be stretched and immediately applied to the suture 502 following and/or during stretching. Stretching the ribbon 504 may involve modifying a structure of the ribbon 504 (e.g., forming ePTFE from PTFE). In some instances, the ribbon 504 may be stretched at least partially through use of thermal processing. For example, a PTFE ribbon 504 may be stretched and/or modified to form ePTFE by applying temperatures within a range of 35-320° C. The ribbon 504 may be at least partially restrained within a stretching device (e.g., a spool) to cause stretching at rates varying from about 10% per second to about 100% per second. The ribbon 504 may be non-elastic due to stretching procedures (e.g., thermal processes) which may be configured to fix molecules of the ribbon 504 in place.

In some instances, the ribbon 504 may be treated to cause adhesion of the ribbon 504 to the suture 502. For example, treating the ribbon 504 may involve applying heat to the ribbon 504. The suture 502 may be twisted during and/or after heat treatment to secure the ribbon 504 to itself (e.g., to the ribbon 504) and/or to the suture 502. The ribbon 504 may be thermally processed to attach the ribbon 504 to itself (e.g., to the ribbon 504) and/or to the suture 502. Once the suture 502 is at least partially encapsulated by the ribbon 504, the suture 502 may be configured to be twisted and/or otherwise assembled into various forms including the knot anchor (see, e.g., knot anchor 190 of FIG. 3) form described previously. The ribbon 504 may be configured not to delaminate from the suture 502 before and/or after formation of the suture 502 into various forms including knots.

The width 505 and/or thickness of the ribbon 504 may vary. In some instances, the ribbon 504 have a relatively wide structure to minimize a number of windings around the suture 502. In this way, the potential for gaps to form between windings of the ribbon 504 may be minimized. However, the windings of the ribbon 504 may be at least partially overlapped to allow the ribbon 504 to adhere not only to the suture 502 but to itself (e.g., the ribbon 504) as well. In some instances, the width 505 of the ribbon 504 may be reduced to increase a number of windings to maximize adhesion of the ribbon 504 to itself (e.g., to the ribbon 504).

Figure 6A:
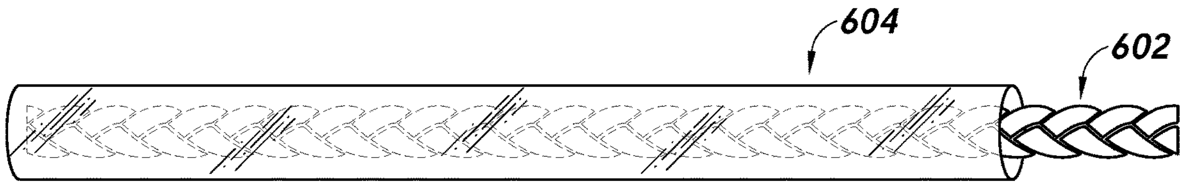
FIGS. 6A and 6B show additional examples of coated sutures in accordance with one or more examples.
Figure 6B:
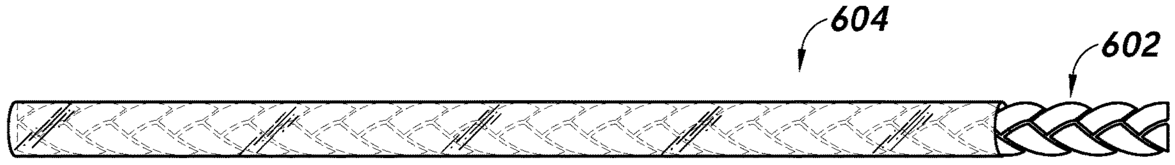

FIGS. 6A and 6B show additional examples of devices comprising coated sutures. In some instances, a coating comprising a tubing 604 may be placed around at least a portion of a suture 602. The tubing 604 may have a generally thin structure to minimize an increase in diameter of the suture 602. For example, the tubing 604 may have a thickness of approximately 75-250 μm (about 0.003-0.01 inches). In some instances, the tubing 604 may be at least partially composed of a polymer. The tubing 604 may be configured to shrink and/or otherwise attach to the surface of the suture 602. For example, the tubing 604 may be configured to be thermally and/or chemically processed to shrink inwardly and/or form a mechanical attachment to the suture 602.

In some instances, a coating may be applied to the suture 602 in other ways. For example, the suture 602 may be configured to be dipped and/or otherwise coated with a liquid and/or viscous high-concentration coating (e.g., a polymer solution). Examples of coatings which a suture 602 may be dipped into can include zwitterionic polymers, such as poly(methacryloyloxylethyl phosphorylcholine), poly (sulfobetaine methacrylate), and poly(sulfobetaineacrylamide). When the suture 602 is coated with the coating, the coated suture may be dried under a vacuum to allow the coating to solidify.

For example, a tubing 604 having a wall thickness of approximately 25-75 μm (about 0.001-0.003 inches) may be extruded from a hydrogel-based polyether polyurethane (e.g., TECOPHILIC™ HP-150 thermoplastic urethane from Lubrizol). A braided suture 602 may be inserted into the tubing 604. When the suture 602 is situated within the tubing 604, the suture 602 and/or tubing 604 may be submerged into a liquid and/or viscous material (e.g., ethanol; certain TECOPHILIC™ thermoplastic urethanes can be partially soluble in ethanol) that may be configured to cause the tubing 604 to shrink and/or conform to a surface structure of the suture 602 (e.g., the tubing 604 may adopt a braided surface structure). The process of submerging the suture 602 and/or tubing may resemble a heat-shrink process in that the tubing 604 may decrease at least partially in diameter due to thermal processing. However, rather thermal processing, submerging the suture 602 and/or tubing may involve chemical processing to cause a decrease in diameter of the tubing 604.

Figure 7:
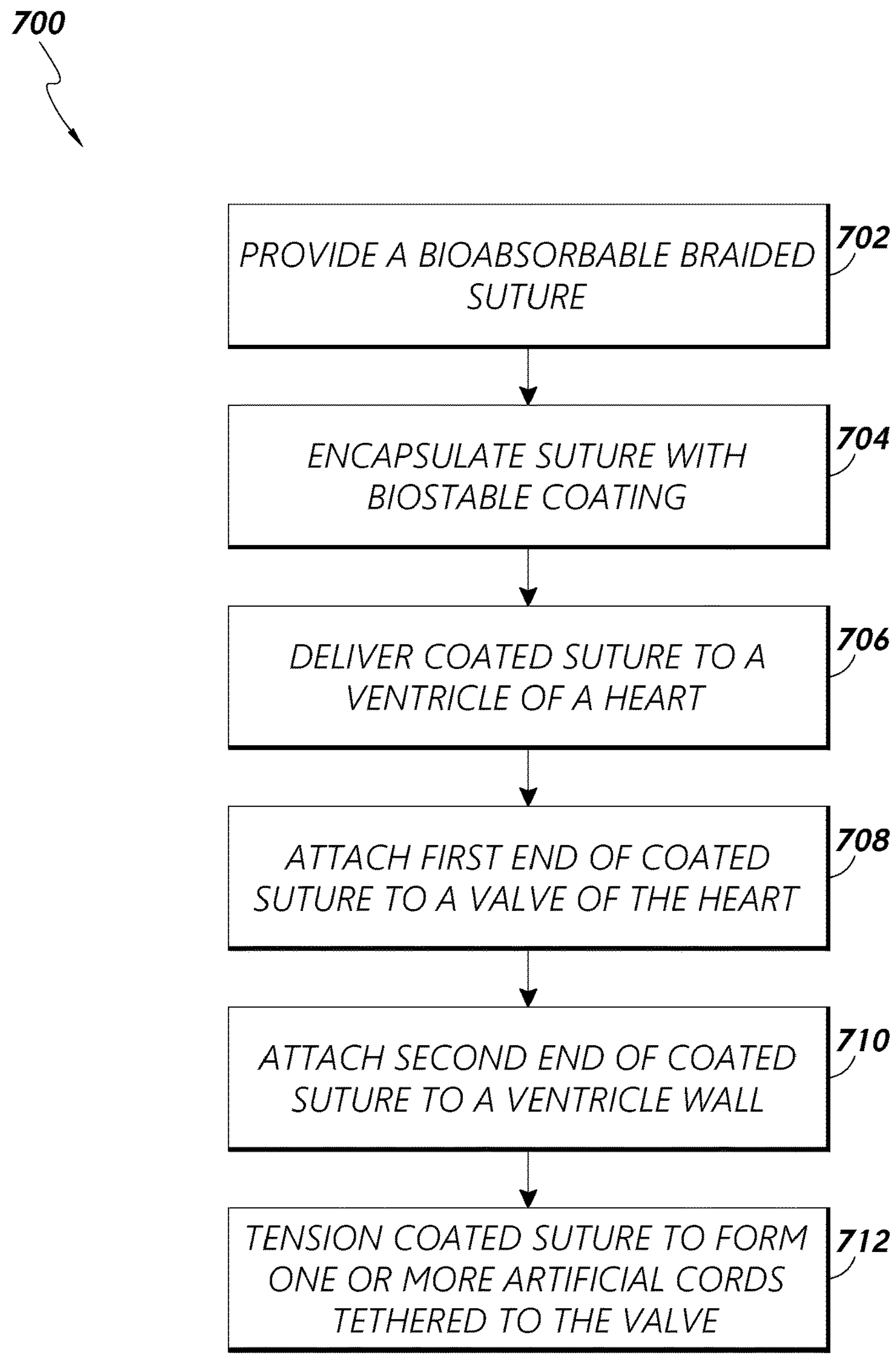
FIG. 7 is a flow diagram illustrating a process for delivering coated sutures into a heart for treating a heart valve in accordance with one or more instances of the present disclosure.

FIG. 7 is a flow diagram illustrating a process 700 for delivering devices (e.g., coated sutures) into a heart for supporting and/or treating a heart valve in accordance with one or more instances of the present disclosure.

At block 702, the process 700 involves providing a suture as described herein, which may include bioabsorbable, bioresorbable and/or biostable braided sutures. The suture may have a generally strong structure and/or may be configured to form secure knots.

At block 704, the process 700 involves encapsulating the suture with a coating material, which can include a biostable coating. The coating may have a form of a ribbon, tube, and/or may comprise a liquid and/or viscous form into which the suture may be dipped to encapsulate the suture.

At block 706, the process 700 involves delivering the coated/encapsulated suture to a ventricle of a heart. For example, the suture may be delivered via an apex region of the heart into the left ventricle for treatment of the mitral valve.

At block 708, the process 700 involves attaching a first end of the coated/encapsulated suture to a valve of the heart. In some instances, attaching the suture may involve passing the suture through an opening in a valve leaflet and/or forming a knot (e.g., a bulky knot) at a distal side of the valve leaflet to prevent the knot portion of the suture from passing back through the valve leaflet.

At block 710, the process 700 involves attaching a second end of the coated/encapsulated suture to a ventricle wall. In some instances, attaching the suture to the ventricle wall may involve passing the suture through an opening in the ventricle wall and/or forming a knot at a distal side of the ventricle wall. The ventricle wall can include an apex region of the heart. In some instances, the suture may be secured to the ventricle wall using a pledget and/or similar device.

At block 712, the process 700 involves tensioning the coated/encapsulated suture to form one or more artificial chords tethered to the valve. In some instances, attaching the suture to the ventricle wall may cause tensioning of the suture.

Figure 8:
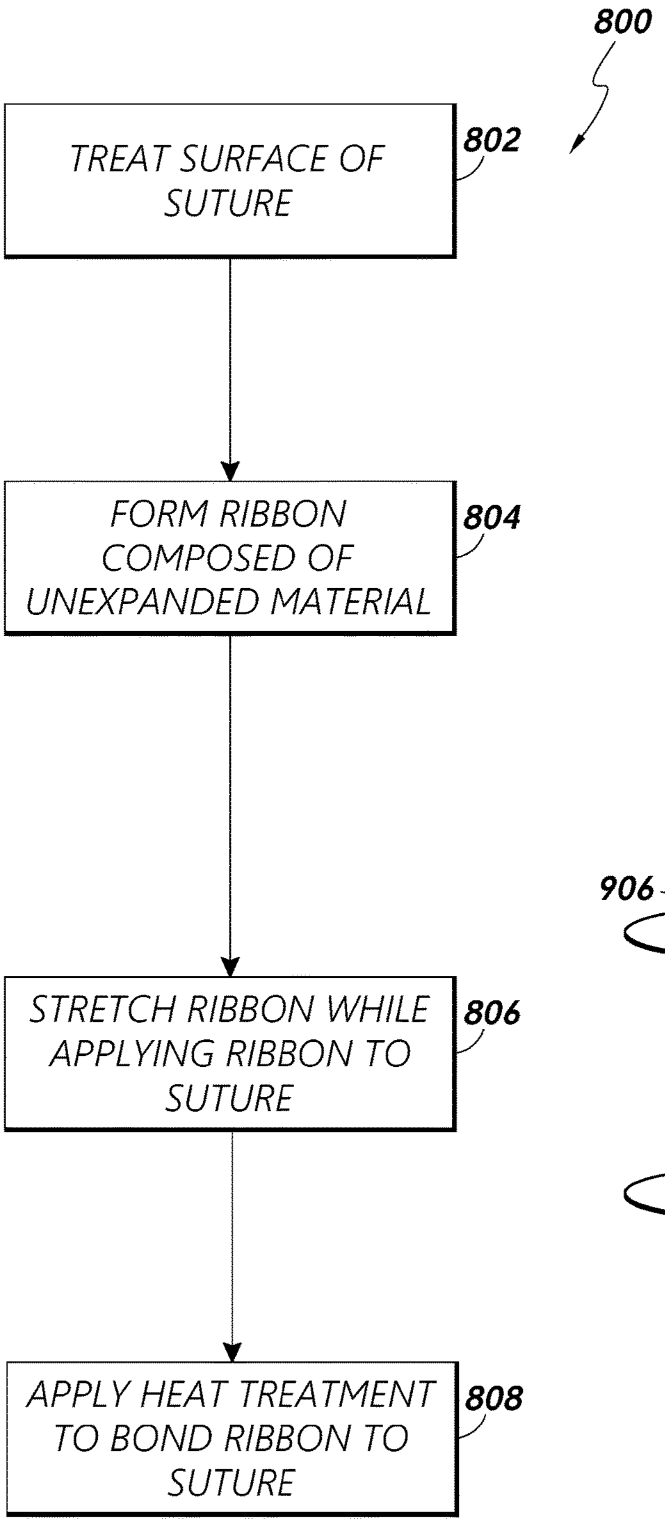
FIG. 8 is a flow diagram illustrating a process for encapsulating a suture with a coating ribbon in accordance with one or more instances of the present disclosure.
Figure 9:
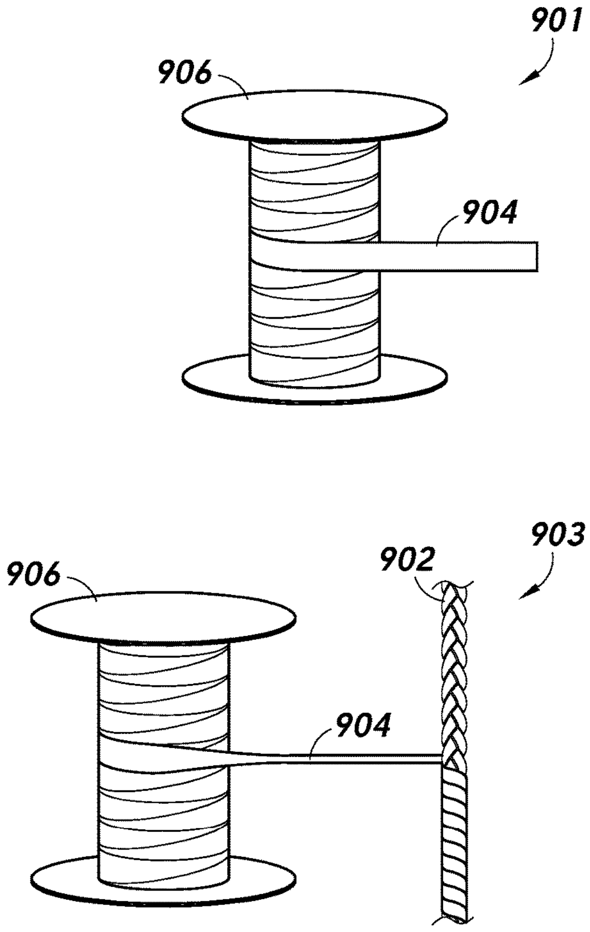
FIG. 9 shows examples of various stages of the process for encapsulating a suture with a coating ribbon shown in FIG. 8.

FIG. 8 is a flow diagram illustrating a process 800 for encapsulating a suture with a coating ribbon in accordance with one or more instances of the present disclosure. FIG. 9 shows examples of various stages of the process 800 for encapsulating a suture with a coating ribbon shown in FIG. 8.

At block 802 of FIG. 8, the process 800 involves treating a surface of a suture to prepare the suture for application of a coating ribbon. Treating the suture may involve plasma and/or corona activation and/or functionalization, chemical cleaning, and/or hydrolyzation, among other possible methods.

At block 804, the process 800 involves forming an unexpanded ribbon from various materials. An example ribbon 904 is shown in image 901 of FIG. 9. The ribbon 904 may be configured to be wrapped around a spool 906 and/or similar device to allow the ribbon 904 to be effectively applied to one or more sutures 902. In some instances, the ribbon 904 may be at least partially composed of unexpanded PTFE. The ribbon 904 may have a generally flat structure with any suitable width.

At block 806, the process 800 involves stretching and/or expanding the ribbon while applying the ribbon to the suture. Image 903 of FIG. 9 shows how a ribbon 904 may be stretched while being removed from a spool 906 and/or may be directly applied to a suture 902. In some instances in which the ribbon 904 is at least partially formed of PTFE, stretching the ribbon 904 may cause the ribbon 904 to form ePTFE. The ribbon 904 may not be required to be stretched and/or expanded prior to the application process. Rather, the ribbon 904 may be applied directly to the suture 902 following and/or during stretching and/or expanding of the ribbon 904. In this way, a separate step of stretching and/or otherwise expanding the ribbon 904 may not be required.

In some instances, stretching and/or expanding the ribbon 904 may be configured to cause alignment of the molecules of the ribbon 904 and/or otherwise increase a tensile strength of the ribbon 904. Moreover, the stretched and/or expanded ribbon 904 may have a more porous structure than in the unexpanded form, which may facilitate healing of tissue around the suture 902 and/or ribbon 904.

At block 808, the process 800 involves applying a treatment to shrink and/or bond/adhere the ribbon to the suture. In some instances, thermal treatment may be used to bond the ribbon to the suture. The ribbon may additionally or alternatively be treated by twisting the ribbon and/or suture and/or by submerging the suture and/or ribbon into a chemical (e.g., ethanol) to cause shrinking of the ribbon and/or otherwise cause adhesion between the suture and ribbon.

ADDITIONAL EXAMPLES

Depending on the example, certain acts, events, or functions of any of the processes or algorithms described herein can be performed in a different sequence, may be added, merged, or left out altogether. Thus, in certain instances, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain instances include, while other instances do not include, certain features, elements and/or steps. Thus, such conditional language is not generally intended to imply that features, elements and/or steps are in any way required for one or more instances or that one or more instances necessarily include logic for deciding, with or without author input or prompting, whether these features, elements and/or steps are included or are to be performed in any particular instance. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain instances require at least one of X, at least one of Y and at least one of Z to each be present.

It should be appreciated that in the above description of instances, various features are sometimes grouped together in a single instance, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular instance herein can be applied to or used with any other instance(s). Further, no component, feature, step, or group of components, features, or steps are necessary or indispensable for each instance. Thus, it is intended that the scope of the disclosure and claims should not be limited by the particular instances described above but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example instances belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A method of preparing a suture for use in medical treatment, the method comprising:

treating a surface of the suture;

applying a coating to the suture;

during application of the coating to the suture, expanding the coating from an unexpanded form to an expanded form, wherein the coating is more porous in the expanded form than in the unexpanded form; and treating the coating to cause adhesion of the coating to the suture.

2. The method of claim 1, wherein the coating has a form of a ribbon.

3. The method of claim 1, wherein expanding the coating decreases a width of the coating.

4. The method of claim 1, wherein the suture and the coating are at least partially composed of different materials.

5. The method of claim 4, wherein the coating is at least partially composed of polytetrafluoroethylene and wherein the suture is not composed of polytetrafluoroethylene.

6. The method of claim 5, wherein expanding the coating involves modifying the coating to be at least partially composed of expanded polytetrafluoroethylene.

7. The method of claim 1, wherein treating the coating involves applying heat to the coating.

8. The method of claim 1, wherein the suture has a polyfilament structure and comprises multiple braided strands.

9. The method of claim 1, wherein the coating is configured to maintain adhesion to the suture during twisting of the suture.

10. The method of claim 1, wherein the coating has a tubular form.

11. The method of claim 10, wherein treating the coating involves shrinking the coating.

12. A method of preparing a suture for use in medical treatment, the method comprising:

treating a surface of the suture;

applying an expandable coating to the suture;

during application of the expandable coating to the suture, expanding the expandable coating from an unexpanded form to an expanded form, wherein the expandable coating is more porous in the expanded form than in the unexpanded form; and treating the expandable coating to cause adhesion of the expandable coating to the suture.

13. The method of claim 12, wherein the expandable coating has a form of a ribbon.

14. The method of claim 12, wherein the suture and the expandable coating are at least partially composed of different materials.

15. The method of claim 14, wherein the expandable coating is at least partially composed of polytetrafluoroethylene and wherein the suture is not composed of polytetrafluoroethylene.

16. The method of claim 15, wherein the expandable coating modifies to expanded polytetrafluoroethylene in the expanded form.

17. A method of preparing a suture for use in medical treatment, the method comprising:

treating a surface of the suture;

applying a coating to the suture, wherein the coating has a flat ribbon form, wherein applying the coating to the suture involves winding the coating over a surface of the suture; and during application of the coating to the suture, expanding the coating from an unexpanded form to an expanded form, wherein the coating is more porous in the expanded form than in the unexpanded form.

18. The method of claim 17, wherein applying the coating to the suture involves at least partially overlapping the coating with itself to facilitate bonding of the coating.

19. The method of claim 17, further comprising treating the coating to cause adhesion of the coating to the suture.

20. The method of claim 17, wherein the coating has a smaller width in the expanded form than in the unexpanded form.

* * * * *